United States Patent [19]

Staats

[11] 4,312,080
[45] Jan. 26, 1982

[54] MODULAR KNEE FINISHING BLOCK AND METHOD OF FINISHING AN ARTIFICIAL LIMB

[75] Inventor: Timothy B. Staats, Mission HIlls, Calif.

[73] Assignee: Regents of University of California, Berkeley, Calif.

[21] Appl. No.: 171,604

[22] Filed: Jul. 23, 1980

[51] Int. Cl.³ .............................................. A61F 1/08
[52] U.S. Cl. .................................................. 3/2; 3/1; 3/21; 3/22; 3/12
[58] Field of Search ..................... 3/1, 2, 12, 17 R, 21, 3/22-29

[56] References Cited

U.S. PATENT DOCUMENTS

| | | | |
|---|---|---|---|
| 1,366,027 | 1/1921 | Savastano | 3/2 |
| 2,478,721 | 8/1949 | Stewart | 3/1.2 |
| 2,480,856 | 9/1949 | enschke et al. | 3/1.2 |
| 3,351,955 | 11/1967 | Middleton | 3/22 |
| 3,377,416 | 4/1968 | Kandel | 264/222 |
| 3,414,908 | 12/1968 | Waggott et al. | 3/1 |
| 3,538,516 | 11/1970 | Bailey et al. | 3/21 |
| 3,597,767 | 8/1971 | Prahl | 3/21 |
| 3,820,169 | 6/1974 | Long et al. | 3/22 |
| 3,823,424 | 7/1974 | May | 3/22 |
| 3,982,278 | 9/1976 | May | 3/21 |
| 4,064,569 | 12/1977 | Campbell | 3/21 X |

FOREIGN PATENT DOCUMENTS 1274616 9/1961 France ........................................ 3/21

OTHER PUBLICATIONS

Manual of United States Mfg. Co., "Hydra-Cadence Guide Book".
Brochure of United States Mfg. Co., "Endoskeletal Prosthetic Systems", pp. 52-59.

Primary Examiner—Ronald L. Frinks
Attorney, Agent, or Firm—Nilsson, Robbins, Dalgarn, Berliner, Carson & Wurst

[57] ABSTRACT

A modular knee finishing block comprising a rigid molded finishing block having an upper and a lower surface and a posterior surface extending between the upper and lower surface, and a tapered surface extending between the upper and lower surface between opposed edges of the posterior surface, and having a knee bracket casting receiving cavity formed in the finishing block and opening into the lower surface and the posterior surface. The receiving cavity has a receiving surface with a plurality of attachment members opening into the receiving surface and each including a passage between the receiving surface and the upper surface. A pair of posterior flexion clearance grooves extend from the receiving surface to the posterior surface. A finishing plug is shaped to conform to the receiving cavity and have a lip sealingly engaging the bottom surface adjacent the receiving cavity, and to conform to the shape of the grooves. An alignment duplication mandrel and alignment plate is used to hold the knee finishing block in an aligned position to duplicate the knee finishing block's alignment in the finished artificial limb.

26 Claims, 13 Drawing Figures

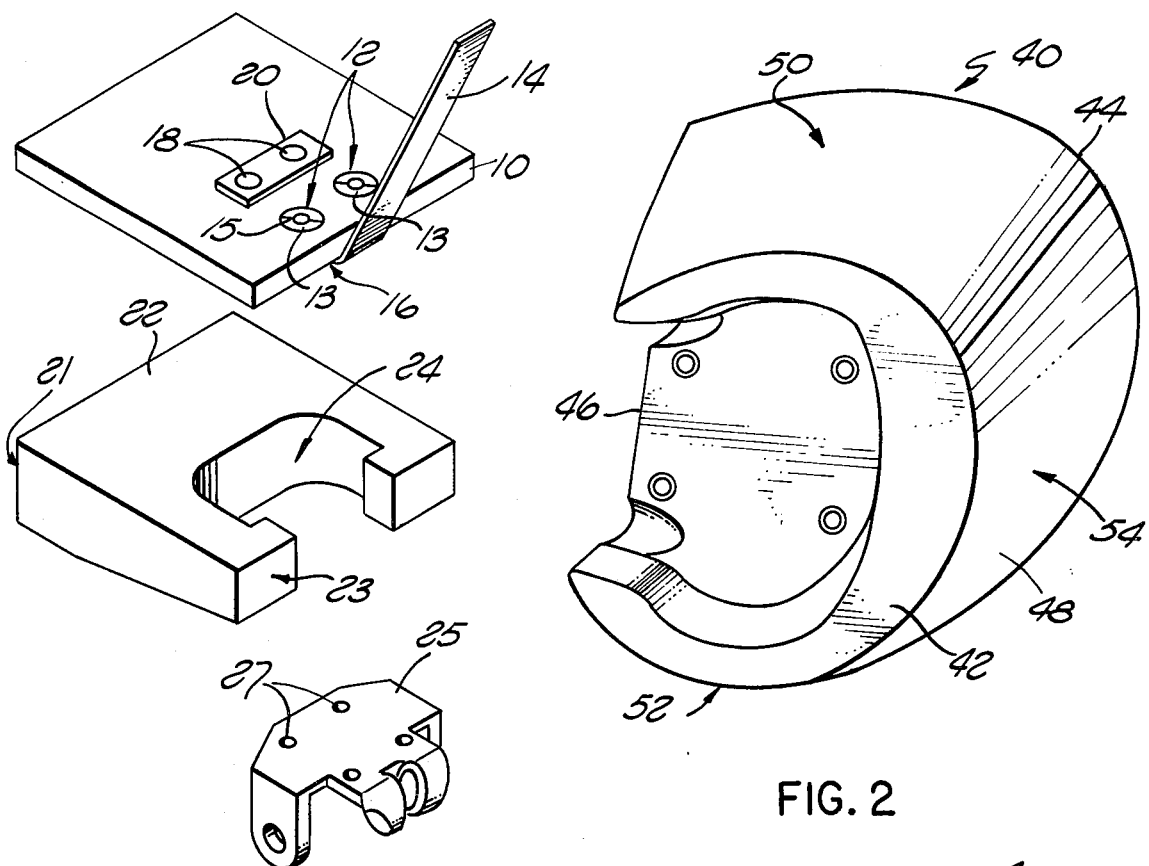
FIG. 2
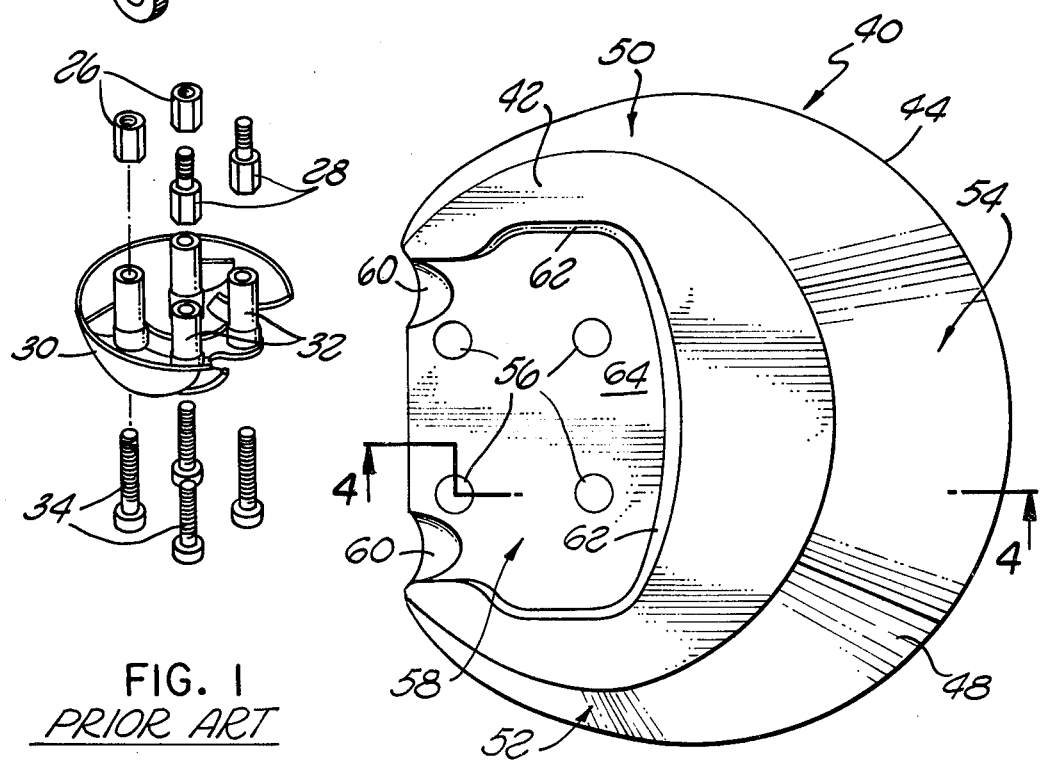
FIG. 1
PRIOR ART
FIG. 3

4,312,080

MODULAR KNEE FINISHING BLOCK AND METHOD OF FINISHING AN ARTIFICIAL LIMB

FIELD OF THE INVENTION

The field of the invention pertains to the field of prosthetic devices, more particularly knee finishing blocks.

BACKGROUND AND SUMMARY OF THE INVENTION

In the past it has been common to supply a wooden knee platform assembly kit along with an artificial limb for above-the-knee amputees. Because the alignment and overall length of the artificial limb are crucial to proper operation, and because each stump socket must be custom made for each individual amputee, the prior art provided this wooden knee platform assembly kit to attach the knee platform to the lower end of the stump socket. Such attachment must be aligned and sized properly for each individual patient. Several such wooden knee platform assemblies are shown in a brochure of United States Manufacturing Company entitled "Endoskeletal Prosthetic Systems" at pages 52–59 attached to the Prior Art Statement filed along with the present application.

The procedure used in the prior art to align and attach the artificial limb knee bracket casting, used for attaching the lower leg portion of the limb containing the mechanical cadence apparatus to the stump socket, is shown, e.g., in a manual of United States Manufacturing Company entitled "Hydra-Cadence Guide Book". A copy of that book is also attached to the Prior Art Statement referred to above.

The pertinent portion of such procedure involves first properly aligning the lower leg cadence portion of the artificial limb to the stump socket on the patient's leg with the patient standing. The above referenced manual shows a wooden stump socket; however, it is now also common to form the socket of a lamination of suitable material, e.g., organic plastic material or hardenable organic polymer foam materials. Steps 11 and 13 at page 18 of the above referenced manual show the artificial limb, with a lower leg cadance portion simulator, in an alignment jig, with an alignment coupling in place. The alignment coupling is a pair of plates, one tripod mounted upon the other. Mechanical means are provided to adjust the distance between the plates and the angles of the plates to custom-fit the lower leg portion of the artificial limb to the stump socket. In the case of the wooden stump sockets shown in the above referenced manual, the lower end thereof is cut flat to receive one plate of the alignment coupling. In the case of currently used laminated or otherwise formed stump sockets, a lower end block is provided to receive the one plate of the alignment coupling. The upper and lower portions of the artificial limb are removed from the jig after certain measurements are recorded with the whole unit in the jig. The above referenced manual shows a horizontal alignment jig; however it is also now common to use a vertical alignment jig, e.g., a Hosmer "Milmo", verticle duplication machine.

The knee bracket casting is then placed on the knee platform. The knee platform is a flat generally rectangular piece of wood having a pair of bolts extending through it from a reinforcing plate and protruding from the lower side thereof. Also attached to the lower side is a socket plate containing receiving sockets for a pair of posterior hex spacers with studs, which screw into a respective one of the receiving sockets. Integral with the socket plate is a metal reinforcing strap.

The knee bracket casting, with the attached cadence mechanical apparatus for the lower leg portion of the artificial limb, is attached to the knee platform by a pair of anterior hex spacers which screw onto the bolts and by the pair of posterior hex spacers with studs which screw into the sockets.

The knee platform and attached cadence mechanism is then placed in an alignment jig, which has been previously set into proper alignment of the lower leg portion of the artificial limb and a stump socket for a particular patient, along with the proper length and foot alignment for that patient as described above with respect to the use of the alignment coupling. The lower leg mechanical portion has also been properly aligned to the knee bracket casting. Once on the jig, the knee platform is then leveled, if necessary, to a 90° angle to the jig horizontal.

The stump socket is then brought into contact with the upper side of the knee platform and the stump socket is trimmed in length as necessary. Thereafter, the outline of the lower end of the stump socket is traced on the knee platform.

The knee platform and stump socket are then removed from the jig and holes drilled through the knee platform for reinforcing screws to attach the knee platform to the stump socket. The knee platform is then glued to the stump socket and the reinforcing screws installed. This procedure of using reinforcing screws is only applicable when the stump socket is made of wood. Currently it is common to use certain suitable rigid urethane foams for the stump socket, in which event no reinforcing screws are used. Certain other steps are then carried out to align the foot portion of the lower leg portion of the artificial limb, which are not pertinent to the present invention.

A spare temporary knee bracket casting is then attached to the bolts and sockets on the lower side of the knee platform and a wooden fairing is put in place onto the lower side of the knee platform. The wooden fairing has a cut-out conforming generally to the outline of the spare knee bracket casting. The wooden fairing is temporarily held in place frictionally, by attaching the plastic knee cap to the knee bracket casting. The knee platform and the fairing are then cut and sanded to conform to the shape of the lower end of the stump socket and, in the case of a wooden stump socket casting, a channel is cut for the metal reinforcing strap which is then screwed into the channel. In the case of urethane foam stump sockets the metal reinforcing strap is attached to the stump socket by embedding it in the foam.

The knee cap and fairing are then removed and grooves are cut using, e.g., a rounded file, in the posterior portion of the knee platform to allow for clearance of the side frames of the cadence mechanism when the artificial limb is flexed. The temporary knee bracket casting must be removed to fully cut and shape the grooves.

The sockets in the knee platform and the extending portions of the bolts in the knee platform are then coated with a lubricant, e.g. silicon, and a piece of stockinette is pulled over the end of the knee platform and stump socket casting making holes for the bolts. The stockinette is painted with a polyester resin over the distal end of the knee platform and for several inches along the stump socket, avoiding coating the bolts. A piece of PVA sheeting is then pulled over the distal end. The PVA sheeting is taped down to insure it conforms to the shape of the previously cut grooves.

The temporary knee bracket casting is then coated with the silicon lubricant and the knee bracket casting, wooden fairing and knee cap are placed in position and secured by the anterior hex spacers, posterior hex spacers with studs and the knee cap screws. Tape is then supplied to further hold the fairing in place and the excess stockinette is cut away, along with the removal of the tape, once the resin hardens.

The knee cap, fairing and temporary knee bracket casting are then detached and the PVA sheeting is removed. Further lubricant, e.g. silicon grease is applied to the temporary knee bracket casting and it is reinstalled on the knee platform. Modeling clay is then applied to the knee platform to provide a seal between the knee platform and the temporary knee bracket casting. The fairing is then placed on the knee platform. The seal prevents later-to-be-applied resin from entering between the knee platform and the knee bracket casting. A clay seal is then formed on the fairing around the circumference of the knee cap, which is then put in place and the excess clay trimmed.

Clay is then used to seal all of the openings in the knee cap plastic piece. Finally a stockinette is put in place over the whole assembly of the stump socket casting and knee platform and knee cap assembly. A PVA bag is pulled over the stockinette and resin poured into the bag to form the stockinette into a hardened smooth outer covering for the upper portion of the artificial limb.

The stockinette is trimmed away from the knee cap area, once the resin hardens, being careful to trim at about one half-inch overlap onto the knee cap and fairing. The knee cap and temporary knee bracket casting are removed. The edges of the fairing are then trimmed and all modeling clay removed from inside the fairing and from the knee cap.

It is thus apparent that the above described procedure is very time consuming and messy. It contains several steps which if improperly carried out could lead to an improper alignment or fit for the artificial limb, necessitating repeating the process. It also involves much skilled labor and the use of large and expensive cutting and wood finishing machinery in the prosthetic laboratory. There is, therefore, a need for a simpler method and apparatus for attaching the lower portion of the artificial limb to the stump socket while still maintaining the proper alignment and sizing.

The problems enumerated in the foregoing are not intended to be exhaustive, but rather are among many which tend to impair the effectiveness of the previously known methods and apparatus for aligning, sizing and finishing the attachment of the stump socket portion to the lower leg portion of an artificial limb for above-the-knee amputees. Other noteworthy problems may exist; however, those presented above should be sufficient to demonstrate that the prior art method and apparatus for aligning sizing and finishing the attachment of the stump socket and lower leg portion of an artificial limb for above-the-knee amputees have not been altogether satisfactory.

The present invention, therefore, relates to a modular knee finishing block. More particularly, the present invention relates to a molded rigid knee finishing block having an upper surface and a lower surface, and a curved tapered surface extending between the upper and lower surfaces and the edges of the posterior surface. A knee bracket casting receiving cavity is formed in the finishing block and has a receiving surface with a plurality of attachment members opening onto the receiving surface and each containing a passage between the receiving surface and the upper surface. A pair of posterior flexion clearance grooves extend from the receiving surface to the posterior surface. A finishing plug conforms to the shape of the cavity and grooves and has a domed surface which assists in shaping the finished outer surface of the upper leg portion of the artificial limb. An alignment duplication mandrel and alignment plate is used to hold the knee finishing block in an aligned position to duplicate the knee block's alignment in the finished artificial leg.

Examples of the more important features of the present invention have thus been summarized rather broadly in order that the detailed description which follows may be better understood, and in order that the contribution to the art may be better appreciated. There are, of course, additional features of the invention that will be described hereinafter and which will form the subject of the appended claims. These other features and advantages of the present invention will become more apparent with reference to the following detailed description of a preferred embodiment thereof in connection with the accompanying drawings wherein like reference numerals have been applied to like elements.

BRIEF DESCRIPTION OF THE DRAWINGS

FIG. 1 shows the prior art knee platform and fairing and the attachment of the spare knee bracket casting and plastic knee cap thereto;

FIG. 2 shows a perspective view of the modular knee block according to the present invention;

FIG. 3 shows a plan view of the bottom, i.e. knee cap side of the modular knee block according to the present invention;

DETAILED DESCRIPTION

Figure 4:
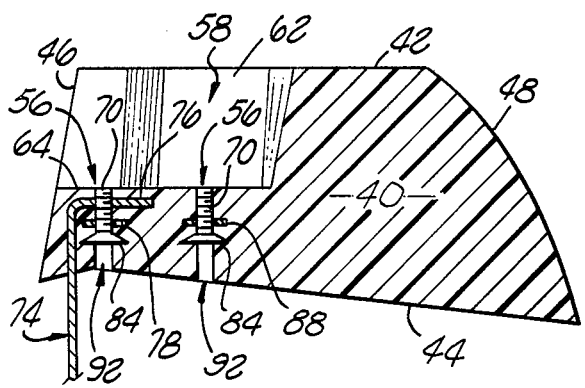
FIG. 4 shows a cross-sectional view of the modular knee block of the present invention along lines 4—4 of FIG. 3.

Turning now to FIG. 1 the knee platform assembly of the prior art is shown to include a knee platform 10 which consists of a flat rectangular piece of wood approximately one-half inch thick. The knee platform 10 has a pair of stud sockets 12 mounted therein. Each stud socket 12 has a broad flat top 13, flush with the top surface of the knee platform 10, and a screwdriving slot 15 in the flat top 13. A reinforcing strap 14 is integrally formed on a strap anchoring plate 16 on the bottom, i.e., knee joint, side of the knee platform 10. The strap reinforcing plate 16 has a pair of threaded openings (not shown) through which the stud sockets 12 pass, into which threads (not shown) on the outer wall of the stud sockets 12 are threaded. A pair of studs 18 also pass through the knee platform 10 and are mounted to a stud anchoring plate 20 on the top side of the knee platform 10.

The fairing 22, discussed above, is a somewhat thicker block of wood, i.e., of about one and one-half inches thick at its maximum at the anterior side 21 thereof, with the bottom side thereof defining a uniform thickness for a portion of the fairing and then a slight taper, terminating at a thickness of about one inch at the posterior end 23 thereof. A knee bracket casting cut-out 24 is formed at the center of the posterior end 23 of the fairing 22.

The spare knee bracket casting 25, as is also discussed above, is formed of an integral piece of metal and is fitted to the knee platform 10, with or without the fairing 22 in place, by a pair of anterior hex spacers 26, which are threaded onto the studs 18, and a pair of posterior studs 28 with hex spacers integrally attached. The molded plastic knee cap 30 is then placed in position with its integrally formed knee cap screw sleeves 32 aligned with the respective one of the hex spacers 26 and posterior hex spacers with studs 28, and knee cap screws 34 are then extended through the sleeves 32 and threaded into internal threads on the anterior hex spacers 26 or on the hex spacers on the posterior studs 28, passing through corresponding holes 27 in the spare knee bracket casting.

The elements of the knee platform assembly are shown in FIG. 1 in order to assist in understanding the above description of the method and apparatus of the prior art.

Turning now to FIGS. 2-4 the modular knee block apparatus of the present invention is shown. A modular knee finishing block 40 is shown to have a bottom surface 42 and a top surface 44. A generally flat posterior surface 46 extends between the top and bottom surfaces 44, 42 at the posterior facing side of the knee finishing block 40. A tapered surface 48 also extends between the bottom and top surfaces 42, 44, tapering towards the bottom surface 42. The tapered surface 48 extends between the opposite side edges of the posterior surface 46 and forms three general regions consisting of a medial surface 50, a lateral surface 52, and an anterior surface 54, assuming the modular knee finishing block 40 of FIGS. 2-4 is for an artificial limb to be placed on the left leg of a patient.

The knee finishing block 40 has a knee bracket casting receiving cavity 58 which opens into the bottom surface 42 and the posterior surface 46, and contains four attachment members 56 which terminate flush against a knee bracket casting receiving surface 64. The knee bracket casting receiving surface 64 is a generally flat surface at the deepest penetration of the knee bracket casting receiving cavity 58 into the knee finishing block 40, i.e., at the terminal end of a cavity wall 62, defining the cavity 58.

A pair of posterior flexion clearance grooves 60 slant upwardly from the knee bracket casting receiving surface and open into the posterior surface 46. These allow for clearance of the side frames (not shown) of the cadence mechanism (not shown) contained in the lower portion of the artificial limb (not shown), when the cadence mechanism is attached by attaching its knee bracket casting to the attaching members 56, and when the artificial limb is in the flexed position. For some currently available cadence units, there is no need for the flexion clearance grooves 60 and they can be, thus, optionally formed in the molded knee finishing block 40.

FIG. 3 shows, in the top view depicted therein, that the cavity wall 62 slants inwardly slightly over most of the circumference of the cavity 58 defined by the cavity wall 62, except for the opposed portions of the cavity wall 62 adjacent the clearance grooves 60. The receiving surface 64 thus has a slightly smaller circumference in the region where the side wall 62 slants inwardly.

Figure 5:
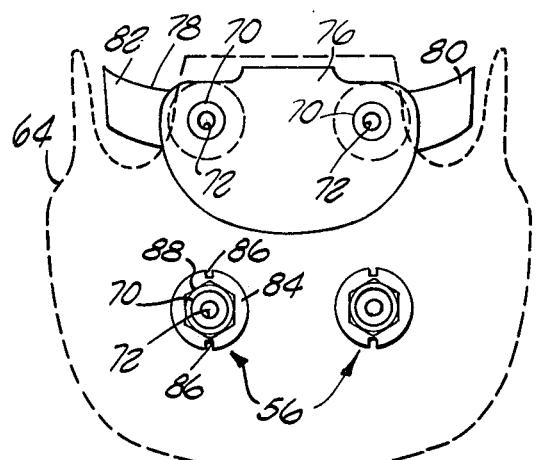
FIG. 5 shows a bottom plan view of the component parts of the knee finishing block imbedded within the rigid molded material of the knee finishing block.
Figure 6:
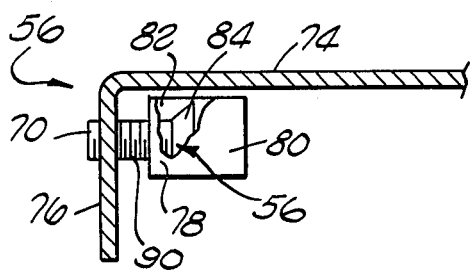
FIG. 6 shows a side view of the component parts as shown in FIG. 5.

FIG. 4 shows in cross-section the components which are imbedded in the knee finishing block 40. Each of the attachment members 56 has a stud socket 70 having internal and external threads, as shown in more detail in FIGS. 5 and 6. FIGS. 5 and 6 show, respectively, a bottom view and a side view of the component parts of the knee finishing block 40 imbedded within the knee finishing block 40. An outline of the knee bracket casting receiving surface 64 is shown in FIG. 5 to assist in visualizing the location of the components shown. The two posterior-most attachment members 56 as shown in FIG. 4 are threaded through one of a pair of holes in a reinforcing strap anchor plate or support plate 76, to which is integrally attached a reinforcing strap 74 which lies just inside the finishing block 40 from the receiving surface 64, with the stud sockets 70 extending through the anchor plate 76 to lie flush with the receiving surface 64. The posterior-most attachment members 56 are also each threaded through one of a pair of holes in a reinforcing bar 78. The attachment member 56 stud sockets 70 each have a head 84 which has an opening therein (not shown) to provide, in conjunction with a passage 92, formed in the knee finishing block 40, an opening between the top surface 44 and the receiving surface 64.

The anterior-most pair of attachment members 56 are each comprised of an identical stud socket 70 having a head 84 with an opening to a passage 92 formed in the finishing block 40. The anterior-most pair of attachment members 56 could also be threaded through a reinforcing bar, similar to reinforcing bar 78. However, they are shown to be optionally provided with additional reinforcement through the threading thereon of a nut 88, as explained in more detail in regard to FIGS. 5 and 6. It will also be understood that reinforcing bar 78 could be replaced by reinforcement through the use of a nut 88, or that nuts 88 could be used on the posterior-most attachment members 56 and a reinforcing bar 78 used on the anterior-most attachment members 56.

The posterior-most attachment member stud sockets 70 are shown to have interior threads. In FIG. 6 the posterior-most stud sockets 56 are shown to pass through the reinforcing strap anchor plate 76 a slight distance equal to the distance which the anchor plate 76 is displaced from the receiving surface 64. The posterior-most stud sockets 70 also are threaded on external threads 90 through a reinforcing bar 78 which has a right wing 80 and a left wing 82, as viewed in FIG. 5. The right and left wings 80, 82 are bent away from the anchor plate 76 to accommodate the locations of the clearance grooves 60 in the finishing block 40. FIG. 6 is partially cut away in the region of the right wing 80 to show the head 84 of the socket stud 70, normally hidden in the side view of FIG. 6.

The view of the anterior-most attachment members 56 in FIGS. 5 and 6 more fully illustrates the construction of the stud sockets 70, of both the anterior-most and posterior-most attachment members 56. The stud sockets 70 of the anterior-most attachment members 56, as well as the posterior-most attachment members 56, have internal threads 72 extending throughout the length thereof. A large flat head 84, having a tapered underside, is formed at one end of the stud sockets 70. The stud sockets were simply chosen for the present invention from available off-the-shelf items, and thus are identical in construction to the stud sockets which come with the knee platform of the prior art shown in FIG. 1. Thus, they have a screw driving slot 86 therein. The anterior most stud sockets 70 are shown to have threaded on the external threads 90 thereof a nut 88.

The knee finishing block 40 of the present invention is composed of a suitable strong rigid thermo-setting plastic material, e.g., a high density polyurethane. A mold is constructed in the shape discussed above and the components shown in FIGS. 5 and 6 are placed in the mold, which has an open top where the top surface 44 of the knee finishing block 40 will ultimately be formed. It will be understood that the particular form of the stud sockets 70 is not crucial to the present invention so long as they will be anchored firmly within the knee finishing block 40 when the thermo-setting material sets. Thus in the form shown in FIGS. 5 and 6, the broad head 84 on each stud socket 70, and the external threads 90 serve to anchor the stud sockets 70 within the hardened material of the knee finishing block 40. The reinforcing bar 78 and nuts 88 are added for further firmly securing the stud sockets 70 within the hardened material, but are optional. As the material hardens around the threads 90 and head 84 of each stud socket 70, sufficient locking of the stud sockets within the hardened material occurs, but for added reinforcement the hardening of the material around the reinforcing bar 78 and/or the nuts 88 is useful. In order to form the passages 92, a stud (not shown) can be placed in each of the stud sockets 70 positioned in the mold prior to adding the thermo-setting material. Each stud is threaded into the opening in the head 84 end of a respective one of the stud sockets 70 and left in that position until the thermo-setting material has firmed up enough to leave a passage 92 when the stud is removed, but not sufficiently to prevent removal of the stud. Removal of the studs at such a time, therefore, leaves the desired passages 92.

Figure 7:
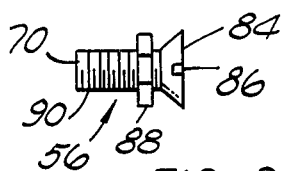
FIGS. 7–12 show schematically the manner of using the method and apparatus of the present invention.
Figure 7:
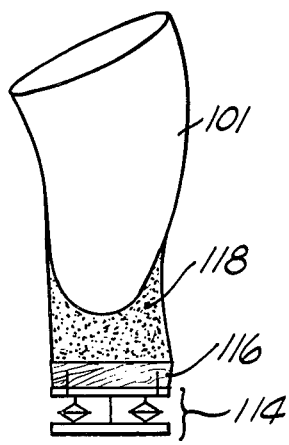

FIGS. 7–13 show the manner in which the present invention is utilized. Referring to FIG. 7, a stump socket 101, formed from a mold of the patient's upper leg stump (as known to the art) is temporarily attached to an alignment coupling 114 (also as known to the art, for example, a Staros-Gardner coupling) which permits the stump socket 101 to tilt or slide in all planes. Normally attachment is accomplished via a wood block 116 screwed to the top surface of the coupling 114 and adhered to the socket 101 with resin or organic polymer foam material 118.

Figure 8:
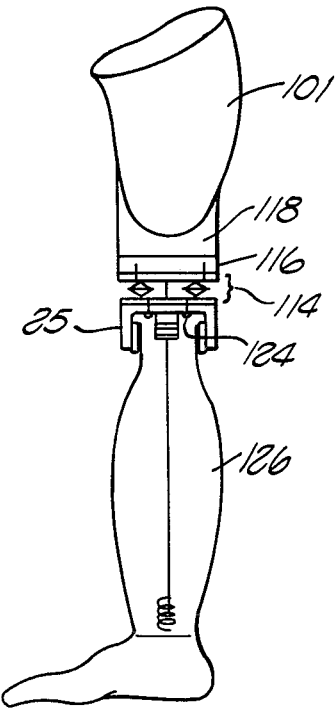

Referring to FIG. 8, once the stump socket 101 is attached to the alignment coupling 114, a knee mechanism 126 is attached to the socket-coupling unit. The knee mechanism 126 includes a knee bracket casting 25, such as shown in FIG. 1 and is attached to the socket 101 with bolts 124 that pass through holes in the knee bracket casting 25. The casting holes align precisely with threaded holes through the alignment coupling 114 and, later, with the knee block holes 56 (FIG. 3).

There is thus provided an entire temporary leg consisting of the stump socket 101, wooden block 116 and resin or foam adhesive 118 therefor, alignment coupling 114 and knee mechanism 126 including the knee bracket casting 25. The patient is then walked on this temporary unit. Alignment changes are made as needed using the alignment coupling 118 and the length of the entire unit is adjusted by substituting a thicker or thinner block 116 and/or adhesive 118 as appropriate.

Figure 9:
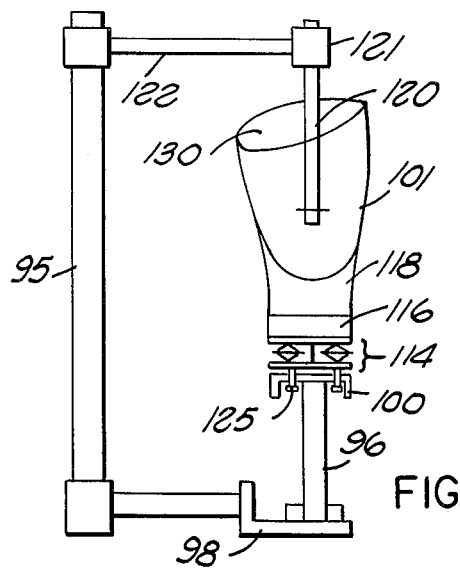

Referring to FIG. 9, when alignment is completed the knee mechanism 126 is removed and a mandrel 96 is attached to the alignment coupling 114. The mandrel 96 includes an upper alignment plate 100 which duplicates in shape the flat portion of the knee bracket casting 25 with correspondingly located stud holes through which bolts 125 are used to secure the mandrel 96 to the alignment coupling 114. The upper alignment plate 100 is shown to comprise a flat plate. It will be understood that it could also be, e.g., a spare knee bracket casting 25 welded, or otherwise attached, to the mandrel 96 to thereby duplicate the flat portion of the knee bracket casting 25 at the upper end of the mandrel 96. The mandrel 96 is shown to be an elongated pipe or bar, and has means at its lower end for attaching the mandrel 96 to an alignment jig 95 as known to the art, e.g., a "Milmo" vertical duplicating apparatus.

The resulting unit is placed in a Milmo apparatus 95 (shown schematically and not fully) and the mandrel 96 is secured to a lower alignment plate 98 of the Milmo apparatus 95 by means of a socket screw and allen wrench (not shown) thereby securing the stump socket 101-coupling 114-mandrel 96 system to the lower end of the Milmo apparatus 95. A pipe 120 is then inserted into a sleeve member 121 carried on the upper arm 122 of the Milmo apparatus so that a substantial length of the pipe 120 extends into the cavity of the stump socket 101. The socket 101 is filled with plaster 130 which, when set, secures the upper Milmo arm 122.

Figure 10:
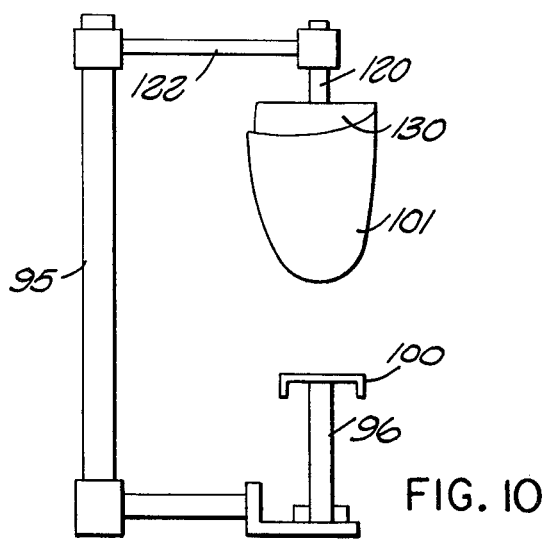

Alignment of the stump socket 101 is now secure. As long as the mandrel 96 and upper alignment plate 100 are not disturbed and as long as the stump socket 101 secured in the plaster 130 is not disturbed, the interconnecting components (i.e. the alignment coupling 114, the wooden block 116 and the resin or foam adhesive 118) can be removed from the system and replaced with the knee block 40 of the present invention to provide a light weight and cosmetic finish. Referring to FIG. 10, the resin or foam adhesive and/or wooden block 116 can be cut away to leave the bottom of the stump socket spaced from and securely suspended over the upper alignment plate 100 of the mandrel 96.

Figure 11:
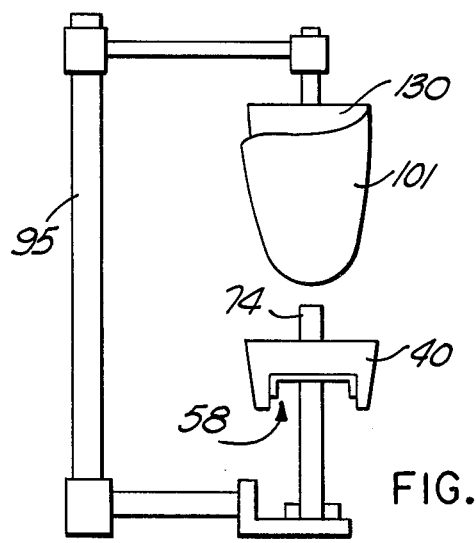

Referring to FIG. 11 as a next step, the finishing block 40 is placed on the upper alignment plate 100 and threaded screws are passed through the upper alignment plate 100, the stud sockets 70 and passages 92 (FIG. 4) in the finishing block 40. The upper alignment plate 100 and a portion of the mandrel 96 extend into the receiving cavity 58.

Figure 12:
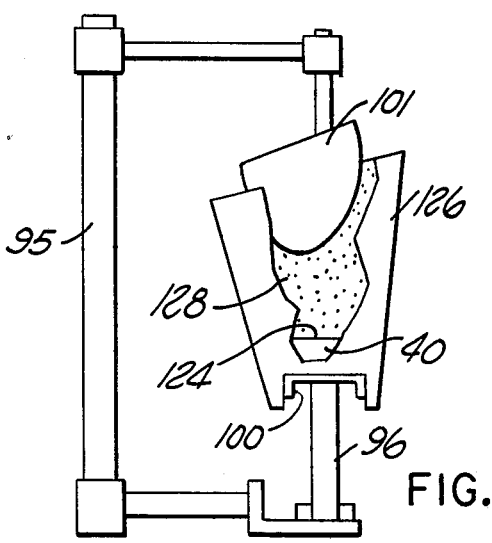

Referring to FIG. 12, a piece of ⅛" thick polyethylene sheeting 126 (shown cut-away) is wrapped around the knee finishing block 40, the vertical dimension of the sheeting 126 extending to encircle a substantial portion of the stump socket 101. Polyurethane foam 128 is poured in liquid form into the space between the socket 101 and sheeting 126 and allowed to foam up and become rigid. To facilitate securement of the polyurethane foam 128 to the knee block 40, prior to pouring the foam liquid, a layer 124 of epoxy adhesive is applied to the upper surface of the knee block.

Figure 13:
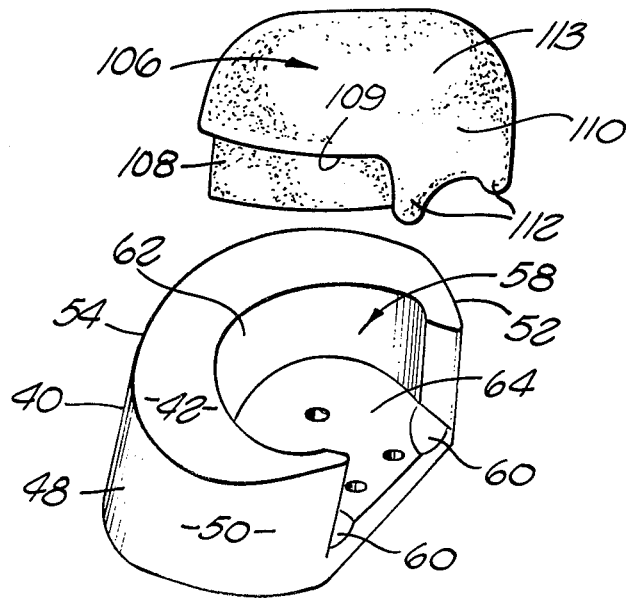
FIG. 13 shows a finishing plug used with the modular knee finishing block of the present invention.

The foamed unit is removed from the Milmo apparatus 95 and is cosmetically shaped to resemble the patient's leg. The mandrel 96 and upper alignment plate 100 are then removed. A finishing plug 106, shown in FIG. 13 is then inserted into the receiving cavity 58. The finishing plug 106 has a plug portion 108 which conform to the shape of the receiving cavity wall 62, receiving surface 64 and grooves 60, and has a lip 109 which extends to the rim of the bottom surface 42 along the lower edge of the lateral, anterior and medial sides 50, 54, 52 of the tapered side 48 of the finishing block 40. This sealingly engages the bottom surface 42. The finishing plug 106 also has posterior wall 110, which when the plug 106 is in place, conforms to the plane of the anterior wall 46. A pair of groove plug members 112 protrude from the edge of the posterior wall 110 and the flat surface of the plug portion 108. The finishing plug 106 is composed of a suitable material, e.g., an elastomeric material to ensure a snug fit within the receiving cavity 58.

A stockinette is then drawn over the finishing plug 106, finishing block 40 and stump socket 101 from the finishing plug 106 and a PVA sleeve is drawn over the stockinette. The stockinette is then hardened by impregnating it with a hardenable resin poured into the PVA sleeve from the stump socket end. The hardened stockinette is trimmed sufficiently to remove the finishing plug 106 and the stump socket and attached finishing block 40 are now ready for attaching the knee bracket casting for the cadence mechanism of the artificial limb by threaded screws inserted into the stud sockets 70 of the finishing block 40 as discussed in relation to FIG. 1. The rounded domed portion 113 of the finishing plug assists in shaping the hardening sockinette and the proper contouring of the lower portion of the stump socket 101 outer shell. The stockinette is hardened to the shape of the knee-cap by conforming to the domed surface 113 of the finishing plug 106 leaving a small lip to enclose the knee cap 30 (FIG. 1).

SUMMARY OF THE ADVANTAGES AND SCOPE OF THE INVENTION

It will be understood that in the modular knee finishing block and method of the present invention certain significant advantages are obtained. A significant reduction in the time and skilled nature of the labor necessary to finish an artificial limb for above-the-knee amputees is achieved. The modular knee block can be pre-molded in varying sizes and supplied along with or separate from the lower leg cadence portions of the artificial limbs. Alternatively, molds can be supplied and prosthetic technicians can fabricate, simply and easily, the knee block of the required size for a given patient, using the mold and the associated hardware components and a thermo-setting material, e.g., high density polyurethane. The mandrel and attached upper alignment plate provide a means for aligning the finishing block to the stump socket.

The foregoing description of the present invention has been directed to a particular preferred embodiment in accordance with the requirements of the present statutes and for purposes of explanation and illustration. It will be apparent to those of ordinary skill in the art, however, that many modifications and changes in both the apparatus and method of the present invention may be made without departing from the scope and spirit of the invention. For example, the particular rigid material used for the modular knee block is disclosed by way of example and other hardenable liquid materials which can be hardened or cured in a mold may also be used.

It will further be apparent that the invention may also be utilized with suitable modifications within the state of the art. Some examples of these include the specific structure of the attachment means disclosed as the stud sockets. The stud sockets, as discussed above, were selected from existing off-the-shelf items. They could be replaced by other attachment means providing a means to connect the finishing block to the simulation of the lower leg cadence portion of the artificial limb on an alignment jig and for attaching the finishing block to the socket stump. Their shape is useful in insuring that they are adequately anchored in an imbedded state in the finishing block material, but other shapes could also easily be selected. The anchoring reinforcement bar and nut serve a similar function of insuring adequate anchoring, but are optional or may be modified in shape, so long as the attachment means components are firmly imbedded within the finishing block. In addition, the present invention has been described in relation to an artificial leg for a human amputee. It will be understood, however, that the invention could also be used for artificial arms and could also be used in veterinary applications.

These and other modifications of the invention will be apparent to those of ordinary skill in the art. It is applicant's intention in the following claims to cover these and other such equivalent modifications and variations as fall within the true spirit of the invention.

What is claimed is:

1. A modular finishing block for an artificial limb comprising:
   a molded rigid finishing block having an upper surface and a lower surface, a posterior surface, joining the upper and lower surfaces, and a curved tapered surface extending between the upper and lower surfaces and the edges of the posterior surface and forming the medial, lateral and anterior surfaces of the finishing block;
   a bracket casting receiving cavity formed in the finishing block and opening in the bottom surface and the posterior surface, and forming a bracket casting receiving surface at the deepest extension of the bracket casting receiving cavity into the finishing block; and
   a plurality of spaced apart attachment members contained within the molded rigid material of the finishing block for attaching a bracket casting of a joint mechanism to the finishing block within the bracket casting receiving cavity.

2. The apparatus of claim 1 in which said attachment members extend through the bracket receiving surface and said upper surface.

3. The apparatus of claim 1, further comprising:
   a pair of posterior flexion clearance grooves slanting upwardly from the bracket casting receiving surface and opening into the posterior surface.

4. The apparatus of claim 1, further comprising:
   a finishing plug having a shape conforming to the bracket casting receiving cavity and having a lip which sealingly engages the bottom surface at the peripheral edge of the opening formed in the bottom surface by the bracket receiving cavity, said finishing plug being detachably mountable on the finishing block.

5. The apparatus of claim 3, further comprising:
   a finishing plug having a shape conforming to the bracket casting receiving cavity including the posterior flexion clearance grooves, and having a lip which sealingly engages the bottom surface at the peripheral edge of the opening formed in the bottom surface by the bracket receiving cavity, said finishing plug being detachably mountable on the finishing block.

6. The apparatus of claim 1, further comprising:
a support plate; and
a reinforcing strap attached to said support plate;
said support plate and a portion of said reinforcing strap being imbedded in the rigid molded material of the finishing block, the remainder of the reinforcing strap extending outwardly of the top surface.

7. The apparatus of claim 1, wherein each attachment member further comprises:
a passage through the finishing block having a threaded inside wall over at least a portion of the passage.

8. The apparatus of any one of claims 1-7 in which said limb is a leg and said finishing block is a knee finishing block.

9. The apparatus of any one of claims 1-7 wherein the finishing block is composed of a thermo-setting plastic.

10. The apparatus of claim 9 wherein said thermo-setting plastic is a high-density polyurethane.

11. A method of duplicating the alignment and finishing of an artificial limb for an above-the-knee amputee comprising the steps of:
attaching a modular knee finishing block of a one-piece molded rigid construction on an aligned simulation mandrel of the lower leg cadence portion of the artificial limb;
aligning a stump socket with the finishing block in opposed relation to the simulation mandrel and attaching the stump socket to the finishing block while maintaining alignment by means of the simulation mandrel attached to the finishing block and an alignment duplication apparatus;
detaching the simulation mandrel;
inserting a finishing plug into a lower leg cadence portion receiving cavity contained within the finishing block, said receiving plug sealingly engaging the peripheral edges of the receiving cavity against intrusion of liquid into the receiving cavity;
placing a stockinette over the assembly of the finishing plug, finishing block and stump socket;
placing a flexible sleeve over the stockinette and pouring a hardenable liquid material into the space between the flexible sleeve and stockinette to impregnate the stockinette;
allowing the hardenable liquid material to harden and removing the flexible sleeve; and
trimming excess hardened impregnated stockinette sufficiently to be able to remove the finishing plug.

12. The method of claim 11 wherein the finishing block is composed of a thermo-setting plastic.

13. The method of claim 12 wherein said thermo-setting plastic is a high density polyurethane.

14. The method of any one of claims 11-13 wherein said hardenable liquid material is a curable liquid resin.

15. An artificial limb finishing system comprising:
a molded rigid finishing block having an upper surface and a lower surface, a posterior surface, joining the upper and lower surfaces, and a curved tapered surface extending between the upper and lower surfaces and the edges of the posterior surface and forming the medial, lateral and anterior surfaces of the finishing block;
a bracket casting receiving cavity formed in the finishing block and opening in the bottom surface casting receiving surface at the deepest extension of the bracket casting receiving cavity into the finishing block;
a plurality of spaced apart attachment members contained within the molded rigid material of the finishing block and extending through the bracket casting receiving surface and the top surface, and including means for attaching the finishing block to a stump socket, for alignment duplication with the stump socket, and for attaching a bracket casting to the finishing block within the bracket casting receiving cavity;
an alignment mandrel, having attached at one end thereof an alignment plate adapted to be inserted into the bracket receiving cavity, the alignment plate including plate attachment members for attaching the alignment plate to the attachment members in the finishing block; and
means for inserting the mandrel and alignment plate into the bracket receiving cavity in an aligned relation to the proper position of the finishing block on the finally formed artificial limb.

16. The system of claim 15 in which said means for attaching the finishing block to a stump socket comprises urethane foam having epoxy adhesive in its contact surface.

17. The system of claim 15 or 16 in which said limb is a leg and said finishing block is a knee finishing block.

18. A method of finishing an artificial knee with a modular knee finishing block formed with a cavity to receive the knee bracket of an artificial limb, comprising the steps of:
aligning a stump socket spaced from a mandrel formed to support said knee finishing block;
placing said knee finishing block on said mandrel;
connecting said stump socket to said knee finishing block;
inserting a finishing plug into the receiving cavity of said knee finishing block;
placing a wrapping over the assembly of finishing plug, knee finishing block and stump socket whereby to conform the lower portion of said wrapping to said finishing plug; and
removing said finishing plug leaving a substantial amount of said conformed wrapping portion.

19. The method of claim 18 in which the bottom of said wrapping is trimmed sufficiently to permit removal of said finishing plug while retaining said substantial amount of conformed portion.

20. The method of claim 18 in which said wrapping comprises a stockinette.

21. The method of claim 20 including the step of impregnating said stockinette with hardenable material whereby to fix said conformity.

22. The method of claim 21 in which said hardenable material is applied by placing a flexible sleeve over the stockinette and pouring said hardenable material as a liquid into the space between said flexible sleeve and said stockinette.

23. The method of claim 21 in which said knee finishing block is of molded one-piece rigid construction.

24. The method of claim 21 including the step of attaching the knee bracket of an artificial limb to the receiving cavity of said knee block.

25. A method of finishing an artificial knee with a modular knee finishing block formed with a cavity to receive the knee bracket of an artificial limb comprising the steps of:

aligning a stump socket spaced from a mandrel formed to support said knee finishing block;

placing said knee finishing block on said mandrel;

connecting said stump socket to said knee finishing block;

inserting a finishing plug into the receiving cavity of said knee finishing block; and attaching the knee bracket of an artificial limb to the receiving cavity of said knee block.

26. The method of claim 25 in which said knee finishing block is of molded one-piece rigid construction.

* * * * *